US00PP36259P2

(12) United States Plant Patent
Neu

(10) Patent No.: US PP36,259 P2
(45) Date of Patent: Nov. 19, 2024

(54) ***PELARGONIUM* PLANT NAMED 'KLEPZ23795'**

(50) Latin Name: ***Pelargonium zonale (L.) L'Hér.* ex *Aiton***
Varietal Denomination: KLEPZ23795

(71) Applicant: KLEMM + SOHN GMBH & CO. KG, Stuttgart (DE)

(72) Inventor: Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/590,360

(22) Filed: Feb. 28, 2024

(51) Int. Cl.
*A01H 5/02* (2018.01)
*A01H 6/42* (2018.01)

(52) U.S. Cl.
USPC ..... Plt./330

(58) Field of Classification Search
USPC ..... Plt./324, 325, 328, 330
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new pelargonium plant particularly distinguished by bright coral flower color; dark green leaf color: very weak leaf zonation; and medium vigor; is disclosed.

1 Drawing Sheet

Genus and species: *Pelargonium zonale* (*L.*) *L'Hér.* ex *Aiton.*

Variety denomination: 'KLEPZ23795'.

BACKGROUND OF THE NEW PLANT

The present invention comprises a new and distinct variety of pelargonium, botanically known as *Pelargonium zonale* (*L.*) *L'Hér.* ex *Aiton* and hereinafter referred to by the variety name 'KLEPZ23795'. 'KLEPZ23795' originated from a controlled cross in August 2018 in Nairobi, Kenya between the commercial female pelargonium variety 'KLEPZ17484' (U.S. Plant Pat. No. 30,335) and the proprietary male pelargonium variety 'PZ-2013-0119' (unpatented).

Seeds from the controlled cross were obtained. The seeds were sown and plants were grown for evaluation. A single plant was selected in June 2019 and subsequently named 'KLEPZ23795'. In July 2019 'KLEPZ23795' was first vegetatively propagated by vegetative stem cuttings in Stuttgart, Germany. 'KLEPZ23795' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Bright coral flower color;
2. Dark green leaf color;
3. Very weak leaf zonation; and
4. Medium vigor.

DESCRIPTION OF THE PHOTOGRAPH

This new pelargonium plant is illustrated by the accompanying photograph which shows an overall view of the plant in a pot. The photograph is of an approximately 20-week-old plant grown indoors in Stuttgart, Germany, in August 2022. The colors shown are as true as can be reasonably obtained by conventional photographic procedures.

DESCRIPTION OF THE NEW VARIETY

The following detailed descriptions set forth the distinctive characteristics of 'KLEPZ23795'. Data was collected on 15-week-old plants in Stuttgart, Germany under greenhouse conditions in February 2024. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium zonale* (*L.*) *L'Hér.* ex *Aiton.*
- *Common.*—Pelargonium.
- *Designation.*—'KLEPZ23795'.

Parentage:
- *Female parent.*—'KLEPZ17484' (U.S. Plant Pat. No. 30,335).
- *Male parent.*—PZ-2013-0119 (unpatented).

Plant:
- *Form.*—Bushy.
- *Habit.*—Upright.
- *Height* (*from top of soil*).—30.0 cm.
- *Width* (*horizontal plant diameter*).—31.0 cm.
- *Natural flowering season.*—March to October.
- *Propagation type.*—Vegetative by stem cuttings.
- *Time to produce a finished flowering plant.*—12 weeks.
- *Time to initiate and develop roots.*—4 weeks.
- *Root description.*—Fine, dense, white, RHS 158A.
- *Flower type.*—Zygomorphic.

Stems:
- *Quantity of stems per plant.*—5-7.
- *Color.*—RHS 143B.
- *Surface texture.*—Pubescent.
- *Stem form.*—Round.

*Diameter.*—0.7 cm.
*Length.*—13.0 cm to 19.0 cm.
*Internode length.*—1.3 cm to 1.5 cm.
*Anthocyanin.*—Present, RHS 178B.

Leaves:
*Arrangement.*—Alternate.
*Shape.*—Reniform.
*Apex.*—Round.
*Base.*—Open.
*Margin.*—Crenate.
*Surface texture both surfaces.*—Both pubescent.
*Length.*—4.3 cm.
*Width.*—7.0 cm.
Color: Upper surface: RHS 139A. Lower surface: RHS N137B.
*Zonation.*—Present but very weak.
*Zonation Color.*—RHS 139A with slightly darker tone than leaf color.
*Depth of Sinus.*—1.0 cm.
*Petiole.*—Length: 4.0 cm. Diameter: 0.3 cm. Color: RHS 143A. Strength: Medium.
*Venation pattern.*—Palmate.
*Venation color.*—Upper surface: RHS 143A. Lower surface: RHS 143A.

Inflorescence:
*Lastingness of flowers on the plant.*—6-8 days.
*Umbels.*—Quantity of umbels per plant: 8-10. Length: 4.7 cm. Diameter: 10.4 cm.
*Individual florets of the umbel.*—Quantity of florets per umbel: 16-20. Depth: 2.4 cm. Diameter: 4.5 cm.
*Fragrance.*—Absent.

Flower buds:
*Cluster shape.*—Round.
*Cluster size.*—Length: 1.7 cm. Width: 2.0 cm.
*Surface texture.*—Pubescent.
*Bud.*—Height: 0.7 cm. Width: 0.6 cm. Shape: Round. Apex: Acute. Base: Obtuse. Margin: Entire. Color: RHS 143A with Anthocyanin shade of RHS 178B.

Petals:
*Quantity per flower.*—7-8.
*Shape.*—Spatulate.
*Apex.*—Round.
*Base.*—Obtuse.
*Margin*—Entire.
*Length.*—3.0 cm.
*Width.*—2.4 cm.
*Surface texture.*—Upper surface: Smooth. Lower surface: Smooth.
*Color of lobes.*—Upper lobes: Upper surface: RHS 52A. Lower surface: RHS 52B. Lower lobes: Upper surface: RHS 52A. Lower surface: RHS 52B.
*Markings.*—Present, darker veins RHS 50A.

Petaloids:
*Quantity per flower.*—1-7.
*Shape.*—Crippled many shapes from lanceolate to flame like.
*Apex.*—Round or acute.
*Base.*—Obtuse.
*Margin.*—Entire.
*Length.*—0.5 cm to 2.0 cm.
*Width.*—0.2 cm to 1.0 cm.
*Surface texture.*—Upper surface: Smooth. Lower surface: Smooth.
*Color.*—Upper surface: RHS 52A. Lower surface: RHS 52B.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Pubescent.
*Color.*—Upper surface: RHS 46A with RHS 144A at tip. Lower surface: RHS 46A with RHS 144A at tip.
*Length.*—1.2 cm.
*Width.*—0.5 cm.

Pedicel:
*Length.*—2.5 cm.
*Diameter.*—0.2 cm.
*Color.*—RHS 46A.
*Surface texture.*—Pubescent.
*Strength.*—Soft.

Peduncle:
*Length.*—10.5 cm.
*Diameter.*—0.4 cm.
*Color.*—RHS 143A with anthocyanin shade of RHS 178B.
*Texture.*—Pubescent.
*Strength.*—Strong.

Reproductive Organs:
*Stamens.*—Quantity per flower: 2-7. Anther length: 0.1 cm. Filament length: 0.7 cm. Filament color: RHS NN155D with RHS 51B at tip. Pollen amount: Medium. Pollen color: RHS 35A.
*Pistils.*—Number: 1. Stigma color: RHS 45A. Style length: 0.4 cm. Style color: RHS 45A. Ovary arrangement: Central Ovary color: RHS 46A. Ovary diameter: 0.2 cm. Ovary length: 0.5 cm. Ovary Texture: Pubescent.

Fruit and seed set: None observed.
Disease and pest/insect resistance: None observed.

COMPARISON WITH PARENTAL LINES AND KNOWN VARIETY

'KLEPZ23795' is distinguished from its parents as described in Table 1.

TABLE 1

Comparison with Parental Lines

| Characteristic | 'KLEPZ23795' | Female parent | Male parent |
|---|---|---|---|
| Flower color | Bright coral | Dark red | White |
| Leaf zonation | Very weak | Strong | Weak |

'KLEPZ23795' can be compared to the commercial variety 'Calliope L Coral' (patent status unknown). Differences between the two varieties are described in Table 2:

TABLE 2

Comparison with Similar Variety

| Characteristic | 'KLEPZ23795' | 'Calliope L Coral' |
|---|---|---|
| Leaf Color | Dark green | Green |
| Vigor | Medium | Vigorous |
| Flower Color | Bright coral | Coral |

I claim:

1. A new and distinct variety of pelargonium plant named 'KLEPZ23795' as illustrated and described herein.

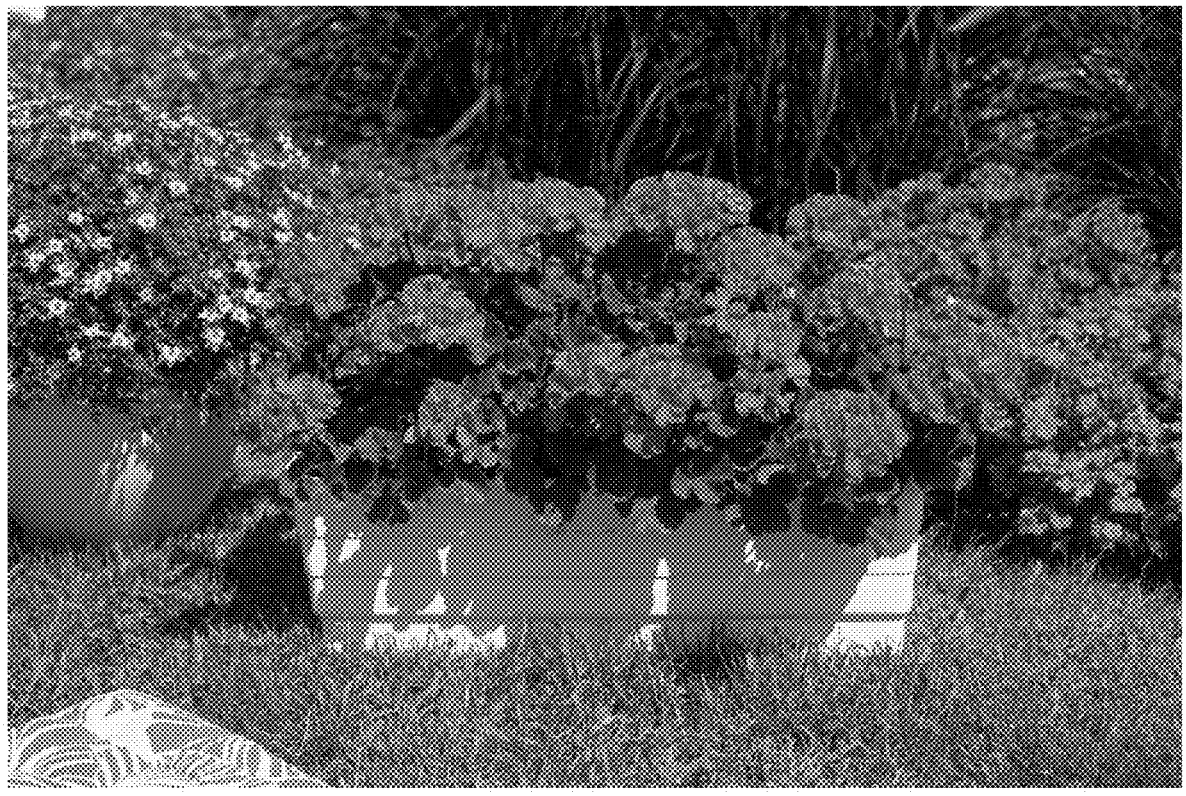

* * * * *